United States Patent [19]

Strayer

[11] Patent Number: 4,493,826
[45] Date of Patent: Jan. 15, 1985

[54] GENTAMICIN-GLEPTOFERRON COMPOSITIONS

[75] Inventor: James G. Strayer, Waterloo, Nebr.

[73] Assignee: Schering Corporation, Madison, N.J.

[21] Appl. No.: 466,998

[22] Filed: Feb. 16, 1983

Related U.S. Application Data

[63] Continuation-in-part of Ser. No. 342,295, Jan. 25, 1982, abandoned.

[51] Int. Cl.³ .................... A61K 35/74; A61K 31/70; A61K 31/71
[52] U.S. Cl. .................................. 424/118; 424/180; 424/181
[58] Field of Search ........................ 424/180, 181, 118

[56] References Cited

U.S. PATENT DOCUMENTS 3,091,572  5/1963  Luedemann et al. ............... 424/118
3,536,696  10/1970  Alsop et al. ......................... 424/180

Primary Examiner—Jerome D. Goldberg
Attorney, Agent, or Firm—Warrick E. Lee, Jr.; Serle Ian Mosoff; Bruce M. Eisen

[57] ABSTRACT

Stable pharmaceutical compositions comprising gentamicin and gleptoferron prevention of iron deficiency anemia and bacterial infections in young mammals, especially piglets.

16 Claims, No Drawings

GENTAMICIN-GLEPTOFERRON COMPOSITIONS

This is a continuation-in-part of my previous U.S. application Ser. No. 342,295, filed Jan. 25, 1982 now abandoned.

The present invention relates to stable injectable pharmaceutical compositions comprising gentamicin and gleptoferron. Gleptoferron is a macromolecular complex of betaferric oxyhydroxide and dextran glucoheptonic acid with an average molecular weight of approximately two million. The molecular formula of gleptoferron may be written $$(FeOOH)_m[(C_6H_{11}O_6)(C_6H_{10}O_5)_n(C_7H_{13}O_7)]_x$$

Under modern commercial rearing conditions, piglets are particularly susceptible to iron deficiency anemia and to a variety of bacterial infections which result in substantial economic loss.

The compositions of the present invention prevent iron deficiency anemia in piglets while also providing a prophylactic effect against bacterial infections, for example, colibacillosis. They may similarly be beneficial for other young mammals that are susceptible to iron deficiency anemia, for example, calves.

Administration of ferric hydroxide complexes of dextran glucoheptonic acid in the treatment of anemia and the preparation of these materials is disclosed in U.S. Pat. No. 3,536,696, the disclosure of which is hereby incorporated herein by reference.

The compositions of the present invention provide stable formulations that may be conveniently stored and used, as desired, to administer two valuable pharmaceuticals in one injection, resulting in considerable cost savings. The compositions of the present invention are surprisingly stable in view of the tendency of iron to deactivate gentamicin.

The compositions of the present invention comprise (a) about 1 to 10 milligrams per milliliter of gentamicin, preferably about 4 to 7 milligrams per milliliter of gentamicin, the gentamicin prefereably being present as the sulfate; (b) about 250 to 1000 milligrams per milliliter of gleptoferron, preferably about 500 to 1000 milligrams per milliliter of gleptoferron and (c) water. The formulations of the present invention may also contain a preservative, for example, phenol.

The ratio of gentamicin to gleptoferron in the compositions of the present invention is not critical, but the amount of each should be within the above limitations.

The formulations of the present invention provide about 50 to 200 milligrams per milliliter of elemental iron, preferably about 100 to 200 milligrams per milliliter of elemental iron. The required amounts of gleptoferron set forth above are calculated based on the fact that the gleptoferron complex is 20 percent iron.

The compositions of the present invention should be administered as one milliliter intramuscular injections to pigs at an age of one to three weeks, preferably when the pigs are one week old. They may be similarly administered to other young mammals.

EXAMPLE 1

An injectable formulation may be prepared by adding 500 mg of gentamicin sulfate to 100 milliliters of gleptoferron injectable solution. Gleptoferron solution is available from Schering Corporation as Heptomer ®.

The resulting composition has the following constituents:

|  | Milligrams/Milliliter |
| --- | --- |
| Gentamicin | 5.0 |
| Elemental Iron (as gleptoferron) | 200 |
| Phenol | 5.0 |
| Water for injection | q.s. 1 ml |

EXAMPLE 2

An injectable formulation similar to that of Example 1 is prepared having the following constituents:

|  | Milligrams/Milliliter |
| --- | --- |
| Gentamicin | 5.7 |
| Elemental Iron (as Gleptoferron) | 200.0 |
| Phenol | 5.0 |
| Water for Injection | q.s. 1 m.l. |

Samples of this formulation are stored under refrigeration, at room temperature and at 35° C. for three months. After storage the samples are analyzed for gentamicin content with the following results.

| Storage Conditions | Gentamicin, mg/ml | Percent Decrease Based on Original Amount |
| --- | --- | --- |
| Refrigeration | 5.6 | 1.8 |
| Room Temperature | 5.1 | 10.5 |
| 35° C. | 4.7 | 17.5 |

COMPARATIVE EXAMPLE A

Several dilute solutions of gentamicin sulfate were stored in rusted containers at 25° C. and 37° C. After 48 hours of storage all of the solutions were found to have decreased gentamicin content. The decreases in gentamicin content varied from 70 to 85 percent. This example clearly shows that iron has a strong tendency to deactivate gentamicin.

COMPARATIVE EXAMPLE B

An injectable formulation is prepared using an iron containing compound tradenamed DEXTRAN, which is a complex of ferric hydroxide with polymers of glucose described in U.S. Pat. Nos. 2,820,740 and 2,885,393.

This composition has the constituents:

|  | mg/ml |
| --- | --- |
| Gentamicin | 5.5 |
| Elemental Iron (as DEXTRAN) | 100.0 |
| Phenol | 5.0 |
| Water for Injection | q.s. 1 ml |

After three months storage samples are analyzed for gentamicin with the following results:

| Storage Conditions | Gentamicin, mg/ml | Percent Decreased Based on Original Amount |
|---|---|---|
| Refrigeration | 5.1 | 7.3 |
| Room Temperature | 4.7 | 14.5 |
| 35° C. | 4.0 | 27.3 |

Notice that the decrease in gentamicin content of comparative Example B is significantly higher than that of Example 2, which is in accordance with the present invention. Notice that the significantly higher decrease in gentamicin in comparative Example B occurred despite its containing only half the elemental iron of Example 2, and despite this iron's being in complex form similar to that of gleptoferron. This clearly shows that the present invention containing gleptoferron achieves a surprisingly high degree of stability.

I claim:

1. A stable injectable pharmaceutical composition comprising (a) about 1 to 10 milligrams per milliliter of gentamicin, (b) about 250 to 1000 milligrams per milliliter of gleptoferron containing iron and (c) water; wherein the weight ratio of iron to gentamicin is about 40 to 1.

2. A composition according to claim 1, also comprising an effective amount of a pharmaceutically acceptable preservative.

3. A composition according to claim 1, wherein the amount of gentamicin is aout 4 to 7 milligrams per milliliter.

4. A composition according to claim 1, wherein the amount of gentamicin is about 4 to 7 milligrams per milliliter and the composition also comprises an effective amount of a pharmaceutically acceptable preservative.

5. The composition of claim 1 wherein the gentamicin is present as gentamicin sulfate.

6. The composition of claim 2 wherein the gentamicin is present as gentamicin sulfate.

7. The composition of claim 3 wherein the gentamicin is present as gentamicin sulfate.

8. The composition of claim 4 wherein the gentamicin is present as gentamicin sulfate.

9. The composition of claim 1 wherein the amount of gleptoferron is 500 to 1000 milligrams per milliliter.

10. The composition of claim 2 wherein the amount of gleptoferron is 500 to 1000 milligrams per milliliter.

11. The composition of claim 3 wherein the amount of gleptoferron is 500 to 1000 milligrams per milliliter.

12. The composition of claim 4 wherein the amount of gleptoferron is 500 to 1000 milligrams per milliliter.

13. The composition of claim 1 wherein the amount of gleptoferron is about 500 to 1000 milligrams per milliliter and the gentamicin is present as gentamicin sulfate.

14. The composition of claim 2 wherein the amount of gleptoferron is about 500 to 1000 milligrams per milliliter and the gentamicin is present as gentamicin sulfate.

15. The composition of claim 3 wherein the amount of gleptoferron is about 500 to 1000 milligrams per milliliter and the gentamicin is present as gentamicin sulfate.

16. The composition of claim 4 wherein the amount of gleptoferron is about 500 to 1000 milligrams per milliliter and the gentamicin is present as gentamicin sulfate.

* * * * *